US006320028B1

(12) United States Patent
Konwinski

(10) Patent No.: US 6,320,028 B1
(45) Date of Patent: Nov. 20, 2001

(54) SOY ISOFLAVONE CONCENTRATE PROCESS AND PRODUCT

(75) Inventor: Arthur H. Konwinski, Fort Wayne, IN (US)

(73) Assignee: Central Soya Company, Inc., Fort Wayne, IN (US)

( * ) Notice: Subject to any disclaimer, the term of this patent is extended or adjusted under 35 U.S.C. 154(b) by 0 days.

(21) Appl. No.: 09/729,999

(22) Filed: Dec. 4, 2000

Related U.S. Application Data

(63) Continuation-in-part of application No. 09/169,896, filed on Oct. 12, 1998, now Pat. No. 6,225,993.
(60) Provisional application No. 60/062,046, filed on Oct. 15, 1997.

(51) Int. Cl.$^7$ .............................. A23J 1/14; A23G 1/02; A23L 1/28; C07D 311/04; A01N 37/18
(52) U.S. Cl. ........................ 530/378; 426/44; 426/46; 426/429; 426/431; 426/439; 426/490; 426/520; 530/378; 549/403; 514/21
(58) Field of Search ........................ 426/634, 429, 426/431, 490, 520, 472, 44, 46, 439; 549/403; 530/378; 514/2

(56) References Cited

U.S. PATENT DOCUMENTS

| | | | |
|---|---|---|---|
| 3,870,805 | 3/1975 | Hayes et al. | 426/656 |
| 4,264,509 | 4/1981 | Zilliken | 260/345.2 |
| 4,366,082 | 12/1982 | Zilliken | 435/125 |
| 4,390,559 | 6/1983 | Zilliken | 426/545 |
| 4,428,876 | 1/1984 | Zilliken | 260/123.5 |
| 5,141,746 | 8/1992 | Fleury et al. | 424/195.1 |
| 5,320,449 | 6/1994 | Shen et al. | 435/68.1 |
| 5,352,384 | 10/1994 | Shen et al. | 252/398 |
| 5,637,562 | 6/1997 | Shen et al. | 514/2 |
| 5,670,632 | 9/1997 | Chaihorsky | 536/8 |
| 5,679,806 | 10/1997 | Zheng | 549/403 |
| 5,702,752 | 12/1997 | Gugger et al. | 426/634 |
| 5,726,034 | 3/1998 | Bryan et al. | 435/68.1 |
| 5,763,389 | 6/1998 | Shen et al. | 514/2 |
| 5,792,503 | 8/1998 | Gugger et al. | 426/634 |
| 5,821,361 | 10/1998 | Waggle et al. | 536/128 |
| 5,827,682 | 10/1998 | Bryan et al. | 435/68.1 |
| 5,851,792 | 12/1998 | Shen et al. | 435/68.1 |
| 5,855,892 | 1/1999 | Potter et al. | 424/757 |
| 5,858,449 | 1/1999 | Crank et al. | 426/556 |
| 5,919,921 | 7/1999 | Waggle et al. | 536/128 |
| 5,932,221 | 11/1999 | Day | 424/195.1 |
| 5,936,069 | 11/1999 | Johnson et al. | 530/378 |
| 5,952,374 | 9/1999 | Clarkson, Jr. et al. | 514/456 |
| 5,968,516 | 10/1999 | Liu et al. | 424/195.1 |
| 5,990,291 | 11/1999 | Waggle et al. | 536/8 |
| 5,994,508 | 11/1999 | Bryan et al. | 530/378 |
| 6,013,771 | 1/2000 | Shen et al. | 530/378 |
| 6,015,785 | 1/2000 | Shen et al. | 514/2 |
| 6,020,471 | 2/2000 | Johns | 536/8 |
| 6,033,714 | 3/2000 | Gugger et al. | 426/634 |
| 6,083,553 | 7/2000 | Waggle et al. | 426/629 |
| 6,132,795 | 10/2000 | Holbrook et al. | 426/634 |
| 6,140,469 | 10/2000 | Shen et al. | 530/370 |
| 6,146,448 | 11/2000 | Kelly et al. | 95/287 |
| 6,146,669 | 11/2000 | Jones et al. | 426/53 |
| 6,159,715 | 12/2000 | Porter et al. | 435/170 |
| 6,171,638 | * 1/2001 | Gugger et al. | 426/634 |

OTHER PUBLICATIONS

Isoflavones and Their Conjugates in Soy Foods: Extraction Conditions and Analysis by HPLC—Mass Spectrometry; Barnes, Stephen et al.; Agric. Food Chem.; vol. 42, No. 11, pp. 2466–2474 (1994).

The Phytoestrogens, Isoflavones, in Soybean Foods in the American and Asian Diets; Barnes, Stephen et al.; unpublished observations; reprints available from Dr. Stephen Barnes, Department of Pharmacology, University of Alabama at Birmingham; sent to Central Soya Company in Jul. 1991.

Genistein, Daidzein, and Their β–Glycoside Conjugates; Antitumor Isoflavones in Soybeans from American and Asian Diets; Coward, Lori et al.; J. Agric. Food Chem.; vol. 41, No. 11, pp. 1961–1967 (1993).

CRC Critical Reviews in Food Science and Nutrition; vol. 27, Issue 4, p. 230 (1988).

Determination of Isoflavones in Soybean Flours, Proteins, Concentrates, and Isolates; Eldridge, Arthur C.; J. Agric. Food Chem.; vol. 30, No. 2, pp. 353–355 (1982).

Malonyl Isoflavone Glycosides in Soybean Seeds (Glycine max Merrill); Kudou, Shigemitsu et al.; Agric. Biol. Chem.; 55(9), 2227–2233 (1991).

Mass Balance Study of Isoflavones during Soybean Processing; Murphy, Patricia A.: J Agric. Food Chem.; vol. 44, No. 8, pp. 2377–2383 (1996).

Genistin (an Isoflavone Glucoside) and Its Aglucone, Genistein, from Soybeans; Walter, E.D.; The Journal of American Chemical Society; vol. 63, pp. 3273–3276 (Dec. 1941).

Isoflavone and saponin glucosides in Soy hispida; Walz, E.; Annalen der Chemie; vol. 489, pp. 118–155; (1931) (Note: inludes English translation from German).

\* cited by examiner

*Primary Examiner*—Jezia Riley

(57) ABSTRACT

A novel process for making an isoflavone concentrate product from soybeans which includes diluting solubles from alcohol-extracted hexane-defatted soybean flakes to about 10% to about 30% solids, separating undissolved solids from the diluted soy solubles and drying the separated solids to make a product having at least 4% by weight isoflavones. The soy isoflavone concentrate product is then used in a liquid or dry beverage, food or nutritional product.

20 Claims, No Drawings

SOY ISOFLAVONE CONCENTRATE PROCESS AND PRODUCT

This application is a C-I-P of Ser. No. 09/169,896 filed Oct. 12, 1998, U.S. Pat. No. 6,228,993 which claims benefit of Ser. No. 60/062,046 filed Oct. 15, 1997.

FIELD OF THE INVENTION

A novel process for making an isoflavone concentrate product from soybeans which includes diluting solubles from alcohol-extracted hexane-defatted soybean flakes to about 10% to about 30% solids, separating undissolved solids from the diluted soy solubles and drying the separated solids to make a product having at least 4% by weight isoflavones. The soy isoflavone concentrate product is then used in a liquid or dry beverage, food or nutritional product.

BACKGROUND OF THE INVENTION

This invention relates to a process for making an isoflavone concentrate product from soybeans. Isoflavones are a unique class of phytoestrogens—plant hormones—that naturally occur in soybeans.

It is anticipated that consumer demand for soy isoflavones will continue to grow. Scientists have demonstrated that isoflavones have the ability to inhibit cancer cell growth, and some researchers believe that isoflavones may contribute to soy's ability to lower blood-cholesterol levels.

Research shows that soy isoflavones have a wide range of health benefits that include moderating normal symptoms associated with menopause and promoting bone and heart health. It appears that about 100 milligrams of isoflavones (expressed in the glucoside form) are necessary to deliver most of these health benefits. This is about the average amount consumed daily by Asian men and women who have a much lower incidence of heart disease, osteoporosis and uncomfortable menopausal symptoms compared to Western societies.

Some women's health problems during and after middle age are related to a changing hormonal state. Consuming soy isoflavones can help moderate the natural hormonal changes associated with several menopausal and postmenopausal symptoms.

Soy isoflavones are potent antioxidants capable of reducing the amount of LDL-cholesterol (bad cholesterol) that undergoes modification in the body. Entry of the modified LDL-cholesterol into the walls of blood vessels contributes to the formation of plaques. These plaques cause the blood vessels to lose their ability to function normally. Research in both animals and humans shows that ingesting soy isoflavones can help maintain normal blood vessel function.

Soy isoflavones are actively studied for their effects on maintaining and improving bone health. Women can lose up to 15% of their total bone mass in the early years following the onset of menopause. This loss can be quite detrimental, particularly to women who enter menopause with weaker bones. Emerging research shows that isoflavones appear to play a role in both preventing bone loss and increasing bone density.

The principal types of isoflavones found in soybeans are glucones (with sugars) and aglucones (without sugars). Glucones have the glucose molecule attached, and include genistin, daidzin and glycitin. Aglucones are isoflavones without the glucose molecule, and they include genistein, daidzein and glycitein. It is an object of this invention to produce products with the isoflavones genistein, daidzein and glycitein in similar proportions as those found naturally in soybeans when isoflavones are reported in the aglucone form.

The prior art teaches isolating genistin from hexane-extracted soybean flakes. Walter ("Genistin (an Isoflavone Glucoside) and Its Aglucone, Genistein, from Soybeans," *J. of Am. Chem. Soc.*, 63, 3273 (1941)) describes a method involving, among other steps, extracting the flakes with methanol, precipitating with acetone and recrystallizing with ethanol.

U.S. Pat. No. 5,141,746 (Fleury et al.) describes a method for preparing an impure extract of two specific isoflavones daidzin malonate and genistin malonate. Fleury describes a method involving, among other steps, mixing hexane-defatted ground soybeans with 80 percent (%) aqueous methanol, filtering and drying; adjusting pH multiple times with, among other chemicals, hydrochloric acid and sodium hydroxide, and extracting with an organic solvent, such as butanol.

U.S. Pat. No. 5,352,384 (Shen) describes making an aglucone enriched fiber. Shen describes solubilizing isoflavones from soy flour by, among other steps, forming a slurry with an extractant, such as sodium. poasum or calcium hydroxide, to adjust the pH to te proteins' isoelectric point of 6.7–9.7, and reacting the slurry with the enzyme β-glucosidase.

The use of multiple acids/bases and organic solvents to extract isoflavones from soybeans makes it costly to commercially manufacture soy isoflavone products. The use of a number of materials to extract isoflavones increases raw material, equipment and labor costs.

It is apparent that an efficient process for removing isoflavones from soybeans is needed. It also is apparent that a low-cost soy isoflavone concentrate (SIC) product is needed.

The invention does not use other chemicals, such as, acetone, hydrochloric acid or sodium hydroxide, to manufacture the SIC product from soy solubles. Soy solubles are recovered from alcohol-extracted hexane-defatted soybean flakes. These solubles, sometimes called soy "molasses", are desolventized, such that they contain less than 0.5% alcohol, and typically are evaporated to 60% solids.

It was discovered that soy solubles, on average, contain 3.31 milligrams per gram (mg/g) genistin on a wet basis and have a total isoflavone content (i.e., daidzin, glycitin, genistin, mal-daidzin, mal-genistin, daidzein, glycitein, genistein and some unidentified isoflavones) of 8.96 mg/g on a wet basis as determined by high performance liquid chromatography (HPLC). The genistin to daidzin ratio of soybeans is about 1 to 1 and that ratio in soy solubles was found to be about 1–1.5 to 1.

It was further discovered that if the soy solubles are diluted with water to form a slurry and the undissolved solids are removed from the slurry to form a wet "cake", the cake contains a significantly concentrated amount of isoflavones.

It was further discovered that if the soy solubles, which have about 20 mg/g isoflavones on a dry basis, are diluted with water to a certain percent solids and the undissolved solids are separated from the diluted solubles with a certain type of centrifuge that the isoflavone content of the solubles can be concentrated by at least 2 times. It was surprising and unexpected to learn that a product with such a high isoflavone content could be produced from the soy solubles without adjusting the solubles' pH with bases or extracting the solubles with another solvent.

SUMMARY OF THE INVENTION

The invention comprises a novel process for manufacturing a novel soy isoflavone concentrate (SIC) product. The isoflavone content by weight of the SIC product is 8 to 11 times that of soy flour, which typically has about 0.6% by weight isoflavones. More particularly, the SIC product contains at least 4% by weight isoflavones, 20–60% protein, with it typically being at least one-third protein, and a relatively low amount of fiber, with it typically being less than 5% fiber. The SIC product is then used in a liquid or dry beverage, food or nutritional product.

DETAILED DESCRIPTION OF THE INVENTION

The invention comprises a novel process for manufacturing a novel soy isoflavone concentrate (SIC) product. The isoflavone content by weight of the SIC product is 8 to 11 times that of soy flour, which typically has about 0.6% by weight isoflavones. More particularly, the SIC product contains at least 4% by weight isoflavones, 20–60% protein, with it typically being at least one-third protein, and a relatively low amount of fiber, with it typically being less than 5% fiber. The SIC product is then used in a liquid or dry beverage, food or nutritional product.

The steps of the subject invention are: 1) dehulling whole soybeans; 2) flaking the dehulled soybeans; 3) extracting soybean oil from the flaked soybeans with hexane, a solvent; 4) desolventizing the defatted soybean flakes without high heating or toasting to produce "white" flakes; 5) extracting the white flakes with aqueous alcohol; 6) recovering solubles from the extraction; 7) desolventizing (removing alcohol) from the soy solubles; 8) diluting the soy solubles with water to form a slurry; 9) separating the undissolved solids from the slurry to form a cake and 10) drying the wet cake. The general procedure for steps 1 through 3 is well described in the prior art. E.g., "Extraction of Oil from Soybeans," *J. Am. Oil Chem. Soc.*, 58, 157 (1981) and "Solvent Extraction of Soybeans," *J. Am. Oil Chem. Soc.*, 55, 754 (1978).

The first step is the dehulling process in which the soybean hulls are removed from the whole soybeans. The soybeans are carefully cleaned prior to dehulling to remove foreign matter, so that product will not be contaminated by color bodies. Soybeans also are normally cracked into about 6 to 8 pieces prior to dehulling.

The hull typically accounts for about 8% of the weight of the whole soybean. The dehulled soybean is about 10% water, 40% protein, 20% fat, with the remainder mainly being carbohydrates, fiber and minerals.

The second step involves the flaking process. Soybeans are conditioned prior to flaking by adjusting moisture and temperature to make the bean pieces sufficiently plastic. The conditioned bean pieces are passed through flaking rolls to form flakes about 0.01 to 0.012 inches (in.) thick.

In the third step, the soybean flakes are defatted by contacting them with hexane to remove the soybean oil. Soybean oil is used in margarine, shortening and other food and products, and is a good source of lecithin, which has many useful applications as an emulsifier.

A detailed description of the general procedure for steps 4 through 7 is found in U.S. Pat. Nos. 3,365,440 (Circle et al.) and 5,097,017 (Konwinski). These steps generally involve the alcohol process for manufacturing soy protein concentrate (SPC). SPC has been described in commerce as a product containing not less than 70% protein (N×6.25). See A. K. Smith and S. J. Circle, Editors, "Soybeans: Chemistry and Technology, Volume I, Proteins," the AVI Publishing Co., 1973.

In step 4, the hexane-defatted soybean flakes are desolventized—hexane is removed—without toasting to produce white flakes. This is different than conventional soybean oil hexane processes where the flakes are toasted and used for animal feed. Instead of being further processed into SPC, the white flakes can be ground to make soy flour.

In step 5, the white flakes are extracted with 55–75%, typically 60%, by weight aqueous ethanol in a countercurrent (flake to solvent flow) extraction device—extractor. The alcohol to flake ratio is about 5 to 1.

The alcohol extraction removes carbohydrates, including oligosaccharides, from the white flakes, which thereby increases the protein content of the material. A typical sample of soy molasses from the SPC alcohol process was found to contain 7.80, 128.50, 19.45 and 86.79 milligrams/gram (mg/g) glucose, sucrose, raffinose and stachyose, respectively, on a wet basis. Soy molasses also typically contains 7–8% protein on a wet basis.

The description of steps 8 through 10 is summarized in the previous section. In the preferred embodiment of this invention, the diluting, separating, pasteurizing and drying steps are performed in a continuous process.

In step 8, the soy solubles are diluted with water to form a slurry. Cold tap water is preferred source of water for the dilution.

In a preferred embodiment of this invention, the solubles are diluted to about 10% to about 30%, most preferred 18% solids. The slurry's pH being 5.5–6.

It also usually is necessary to provide some agitation or mixing to slurry the diluted solubles. One means for performing the mixing is a propeller-type agitator. The diluted soy solubles may be optionally cooled using a chiller.

In step 9, the undissolved solids are removed from the slurry to form a wet cake. The undissolved solids could be removed by a number of physical separation means; however, centrifugation is the most efficient and effective means.

In the preferred embodiment of this invention, a scroll-type centrifuge is used to remove the undissolved solids from the slurry, such that wet cake is 25–30% solids and contains about 10–20% of the soy solubles' solids. In yet another embodiment of this invention, the separation can be performed with a disc-type or tubular centrifuge.

Alternatively, the dilution and separation steps 8 and 9 could be described as water "washing" the soy solubles. These steps serve to concentrate the soy isoflavones from the solubles. In another embodiment of this invention, the washing process may be repeated one or more times in an effort to further concentrate the isoflavones, however, product yield (the quantity of SIC produced) would decrease.

In a preferred embodiment of this invention the wet cake is pasteurized prior to the drying step 10, so that the SIC will test negative for salmonella and have an acceptable microbial profile. One means for pasteurization is to hold the wet cake in a steam-jacketed kettle for 10 minutes at 160 degrees Fahrenheit (° F.).

In step 10, the wet cake is dried to produce SIC useable as a nutritional supplement, or a food ingredient or product. The preferred means of drying is a vertical spray drier with a high pressure nozzle. To facilitate spray drying, the wet cake is diluted to less than 25% solids, most preferred 15%, prior to pasteurization.

A lot prepared by the above method had 6.9% isoflavones (66.7% genistein, 32.1 % daidzein and 1.2% glycitein when isoflavones are reported in the aglucone form); 32.8% protein; 2.1% fat; 55.6% total carbohydrates; 4.4% moisture and 5.1% ash, with no heavy metals detected. When analyzed for isoflavones using standard HPLC methodology, the lot had 40.7 milligrams/gram (mg/g) genistin; 20.7 mg/g daidzin; 0.8 mg/g glycitin; 1 mg/g daidzein; 0.7 mg/g genistein and 0 glycitein.

Another lot prepared by the above method had 4.5% isoflavones (57.8% genistein; 37.4% daidzein and 4.6% glycitein when isoflavones are reported in the aglucone form); 30.2% protein; 1.3% fat; 59.5% total carbohydrates; 3.8% moisture and 5.2% ash, with no heavy metals detected. When analyzed for isoflavones using standard HPLC methodology, the lot had 23.7 milligrams/gram (mg/g) genistin; 14.3 mg/g daidzin; 2.0 mg/g glycitin; 1.6 mg/g daidzein; 0.04 mg/g genistein and 0 glycitein. These about 4% isoflavone concentrate products typically contain about 10% saponins by weight.

The spray-dried powdered SIC has many uses. For example, it can be tableted or used in drink mixes.

The spray-dried powdered SIC may be coated with commercial lecithin or other food-grade surfactants, such as mono-diglycerides, to improve water dispersibility and reduce clumping of the product. Such a coating-addition would be in the range of about 0.5%.

These and other aspects of the present invention may be more readily understood by reference to one or more of the following examples. These examples illustrate the practice of this invention:

EXAMPLE 1

Solubles with 53.5% solids and 11.6 milligrams/gram (mg/g) total isoflavones on a wet basis were recovered from alcohol-extracted hexane-defatted soybean flakes. The solids content of the solubles was adjusted to approximately 18%, and the resulting slurry was passed through a scroll-type centrifuge at a feed rate of 30 gallons per minute. The cake contained about 27% solids, and was diluted to about 18% solids. It was then pasteurized at 170 degrees Fahrenheit (° F.), and spray dried at a rate of about 400 pounds (lbs.) of dry solids per hour in a vertical spray dryer using pressure nozzles. The spray-dried product contained 6.1% total isoflavones.

EXAMPLE 2

Solubles with 55.9% solids were recovered from alcohol-extracted hexane-defatted white soybean flakes. 150 pounds (lbs.) of the solubles at 38 degrees Fahrenheit (° F.) were mixed with 303 lbs. of cold tap water with a propeller-type mixer to form a slurry of 453 lbs. of material with 17.72% solids at 63° F. The slurry was passed through a Sharples tubular bowl (Model AS-12) scroll-type centrifuge to form 23.35 lbs. of cake with 35.5% solids. The cake was freeze-dried to produce a product with a total isoflavone content of 82.44 milligrams/gram (mg/g).

It will be understood that the claims are intended to cover all changes and modifications of the preferred embodiments of the invention herein chosen for the purpose of illustration which do not constitute a departure from the spirit and scope of the invention.

What is claimed is:

1. A method for making an isoflavone product by separating undissolved solids from solubles from alcohol-extracted hexane-defatted soybeans, with said solids forming said product having at least 4% isoflavones by weight of dry matter and a genistin to daidzin ratio of about 1–3 to 1.

2. The product of claim 1 wherein said product is about 4.5–8.5% isoflavones.

3. The product of claim 1 wherein said genistin to daidzin ratio of said product is about 1.5–2 to 1 and said solubles is about 1–1.5 to 1.

4. The product of claim 1 wherein the genistin to daidzin ratio of said soybeans is about 1 to 1.

5. The product of claim 1 wherein about 55–75% of said isoflavones are genistein; at least 20–40% of said isoflavones are daidzein and less than 5% of said isoflavones are glycitein when said isoflavones are reported in the aglucone form.

6. The product of claim 1 wherein said solubles are at least 50% solids.

7. The product of claim 1 wherein said product is less than 40% protein by weight of dry matter.

8. The product of claim 1 wherein said product is more than 50% carbohydrate by weight of dry matter.

9. The product of claim 1 wherein said product is less than 5% fat by weight of dry matter.

10. The product of claim 1 wherein said product is at least 5–10% saponins by weight of dry matter.

11. A liquid or dry beverage, food or nutritional product that uses the product of claim 1.

12. The product of claim 1 wherein said separation is aqueous.

13. The product of claim 1 wherein said solubles are desolventized.

14. The product of claim 1 wherein said soybeans are flaked.

15. A method for making an isoflavone product by aqueously separating undissolved solids from desolventized solubles from alcohol-extracted hexane-defatted soybean flakes without substantial conversion of daidzin to daidzein, with said solubles having a genistin to daidzin ratio of about 1–1.5 to 1 and said solids forming said product having at least 4% isoflavones by weight of dry matter, about 50% carbohydrate by weight of dry matter, less than 40% protein by weight of dry matter, about 5–10% saponins by weight of dry matter and a genistin to daidzin ratio of about 1.5–2 to 1.

16. A liquid or dry beverage, food or nutritional product that uses the product of claim 15.

17. A method for making a phytochemical product by aqueously separating undissolved solids from alcohol-extracted soy solubles, with said solids forming said product having at least 4% isoflavones by weight of dry matter and at least 4% saponins by weight of dry matter.

18. The method of claim 17 wherein said separation is performed by centrifugation without ultrafiltration or chromatography prior to said centrifugation.

19. The method of claim 18 wherein said solubles are desolventized and are at least 50% solids with a genistin to daidzin ratio of about 1–1.5 to 1, said solubles are diluted with water to about 10–30% solids prior to said centrifugation and said product contains about 10–20% of said solids having about 4.5–8.5% isoflavones by weight of dry matter with a genisrin to daidzin ratio of about 1.5–2 to 1 and about 5–10% saponins by weight of dry matter.

20. A liquid or dry beverage, food or nutritional product that uses the product of claim 17.

\* \* \* \* \*

UNITED STATES PATENT AND TRADEMARK OFFICE
CERTIFICATE OF CORRECTION

PATENT NO. : 6,320,028 B1
DATED : November 20, 2001
INVENTOR(S) : Arthur H. Konwinski It is certified that error appears in the above-identified patent and that said Letters Patent is hereby corrected as shown below:

<u>Title page,</u>
Item [56], References Cited, under OTHER PUBLICATIONS, delete "inludes" and insert -- includes --

Item [74], *Attorney, Agent, or Firm*, insert -- Michael L. Fuelling --

Item [63], patent no. 6,225,993 should read -- 6,228,993 --

<u>Column 2,</u>
Lines 23 & 24, "sodium. poasum, or calcium hydroxide, to adjust the pH to te" should read -- "sodium, potassium, or calcium hydroxide, to adjust the pH to the" --.

Signed and Sealed this

Sixth Day of August, 2002

*Attest:*

*Attesting Officer*

JAMES E. ROGAN
*Director of the United States Patent and Trademark Office*